(12) United States Patent
Ancira

(10) Patent No.: US 6,710,076 B2
(45) Date of Patent: *Mar. 23, 2004

(54) HYDROXY-KOJIC ACID SKIN PEEL

(75) Inventor: Margaret M. Ancira, Scottsdale, AZ (US)

(73) Assignee: Physician's Choice of Arizona, Inc., Scottsdale, AZ (US)

(*) Notice: Subject to any disclaimer, the term of this patent is extended or adjusted under 35 U.S.C. 154(b) by 0 days.

This patent is subject to a terminal disclaimer.

(21) Appl. No.: 09/974,743

(22) Filed: Oct. 9, 2001

(65) Prior Publication Data

US 2002/0082293 A1 Jun. 27, 2002

Related U.S. Application Data

(63) Continuation of application No. 09/299,788, filed on Feb. 22, 1999, now Pat. No. 6,300,369, which is a continuation of application No. 08/795,231, filed on Feb. 10, 1997, now Pat. No. 5,874,463, which is a continuation-in-part of application No. 08/328,006, filed on Oct. 24, 1994, now abandoned.

(51) Int. Cl.[7] .................. A61K 31/35; A61K 31/19; A61K 7/42

(52) U.S. Cl. .................. 514/460; 514/557; 514/574; 424/59; 424/62

(58) Field of Search .................. 514/460, 557, 514/574, 568, 725, 738; 424/59, 62

(56) References Cited

U.S. PATENT DOCUMENTS

| | | |
|---|---|---|
| 3,265,571 A | 8/1966 | Krezanoski |
| 3,666,863 A | 5/1972 | Swanbeck .................. 424/316 |
| 3,806,593 A | 4/1974 | Swanbeck .................. 424/28 |
| 3,856,934 A | 12/1974 | Kligman .................. 424/62 |
| 4,278,656 A | 7/1981 | Nagai et al. .................. 424/62 |
| 4,285,973 A | 8/1981 | Edwards .................. 424/358 |
| 4,294,852 A | 10/1981 | Wildnauer et al. .......... 424/317 |
| 4,318,907 A | 3/1982 | Kligman .................. 424/230 |
| 4,369,174 A | 1/1983 | Nagai .................. 424/62 |
| 4,608,370 A | 8/1986 | Aronsohn .................. 514/159 |
| 4,696,813 A | 9/1987 | Higa .................. 424/59 |
| 4,847,074 A | 7/1989 | Hatae .................. 424/62 |
| 4,874,361 A | 10/1989 | Obagi .................. 604/20 |
| 4,891,361 A | 1/1990 | Hatae .................. 514/58 |
| 4,919,921 A | 4/1990 | Hatae .................. 424/62 |
| 4,948,577 A | 8/1990 | Hara .................. 424/59 |
| 4,985,255 A | 1/1991 | Higa .................. 424/583 |
| 4,985,455 A | 1/1991 | Motono .................. 514/460 |
| 4,990,330 A | 2/1991 | Oyama .................. 424/59 |
| 4,990,532 A | 2/1991 | Yamamoto .................. 514/46 |
| 5,043,356 A | 8/1991 | Fulton, Jr. .................. 514/549 |
| 5,063,056 A | 11/1991 | Yamamoto .................. 424/401 |
| 5,164,182 A | 11/1992 | Meybeck et al. .......... 424/773 |
| 5,164,185 A | 11/1992 | Charpin et al. .......... 424/401 |
| 5,166,176 A | 11/1992 | Obagi et al. .......... 514/557 |
| 5,244,665 A | 9/1993 | Natraj et al. .......... 424/401 |
| 5,262,153 A | 11/1993 | Mishima et al. |
| 5,279,834 A | 1/1994 | Meybeck .................. 424/450 |
| 5,378,455 A | 1/1995 | Kealey et al. .......... 424/73 |
| 5,427,775 A | 6/1995 | Sakai et al. .................. 424/63 |
| 5,443,840 A | 8/1995 | Morancais et al. ........ 424/450 |
| 5,486,624 A | 1/1996 | Yang et al. .................. 549/418 |
| 5,505,948 A | 4/1996 | Rapaport .................. 424/401 |
| 5,520,918 A | 5/1996 | Smith .................. 424/401 |
| 5,523,421 A | 6/1996 | Yang et al. .................. 549/418 |
| 5,531,993 A | 7/1996 | Griat .................. 424/401 |
| 5,540,853 A | 7/1996 | Trinh et al. .................. 510/101 |
| 5,545,407 A | 8/1996 | Hall et al. .................. 424/401 |
| 5,547,678 A | 8/1996 | Gagnebien-Cabanne .... 424/401 |
| 5,560,907 A | 10/1996 | Sakai .................. 424/62 |
| 5,580,549 A | 12/1996 | Fukuda et al. .......... 424/62 |
| 5,599,528 A | 2/1997 | Igaki .................. 424/59 |
| 5,607,692 A | 3/1997 | Ribier et al. .......... 424/450 |
| 5,609,875 A | 3/1997 | Hadas .................. 424/195.1 |
| 5,637,293 A | 6/1997 | Honda .................. 424/62 |
| 5,874,463 A | 2/1999 | Ancira .................. 514/460 |
| 5,989,536 A | 11/1999 | Deckner et al. .......... 424/78.05 |
| 6,197,343 B1 * | 3/2001 | Minami et al. .......... 424/489 |
| 6,300,369 B1 * | 10/2001 | Ancira .................. 514/460 |
| 6,348,200 B1 * | 2/2002 | Nakajima et al. ........ 424/401 |
| 6,348,204 B1 * | 2/2002 | Touzan .................. 424/401 |
| 6,365,137 B1 * | 4/2002 | Aust et al. .................. 424/62 |
| 6,383,523 B1 * | 5/2002 | Murad .................. 424/616 |
| 6,384,079 B1 * | 5/2002 | Yu et al. .................. 514/577 |
| 6,391,863 B1 * | 5/2002 | Philippe et al. .......... 514/62 |
| 6,403,064 B1 * | 6/2002 | Alaluf et al. .......... 424/62 |
| 6,417,226 B1 * | 7/2002 | Perricone .................. 514/474 |
| 6,495,126 B1 * | 12/2002 | Schiltz .................. 424/78.02 |
| 6,534,543 B2 * | 3/2003 | Ptchelintsev et al. ....... 514/558 |
| 6,544,533 B2 * | 4/2003 | Breton et al. .......... 424/401 |
| 6,590,105 B2 * | 7/2003 | Bradley et al. .......... 548/252 |
| 6,616,933 B1 * | 9/2003 | Breton et al. .......... 424/401 |

FOREIGN PATENT DOCUMENTS

| | | |
|---|---|---|
| EP | 308918 | 3/1989 |
| EP | 308919 | 3/1989 |
| EP | 0 345 081 A2 | 12/1989 |
| EP | 0 345 082 A2 | 12/1989 |
| JP | 01121205 | 5/1989 |
| JP | 01275524 | 11/1989 |
| JP | 01311011 | 12/1989 |
| JP | 02028105 | 1/1990 |

(List continued on next page.)

OTHER PUBLICATIONS

Ancira, "Licensed to Peel," Dermascope, 26–27, 1994.
Andrews, "Diseases of the Skin", Philadelphia, WB Saunders, 1928:240–248.
Bendas et al., "Propylene glycol," In: *Percutaneous Penetration Enhancers*, Smith et al., (Eds.), CRS Press, p. 61–77, 1995.

(List continued on next page.)

*Primary Examiner*—Deborah C. Lambkin
(74) *Attorney, Agent, or Firm*—Stinson Morrison Hecker LLP (57) ABSTRACT

The subject of the present invention is a hydroxy-kojic acid skin peel.

101 Claims, 6 Drawing Sheets

FOREIGN PATENT DOCUMENTS

| | | |
|---|---|---|
| JP | 02045408 | 2/1990 |
| JP | 02049709 | 2/1990 |
| JP | 3-236319 | 2/1990 |
| JP | 02142714 | 5/1990 |
| JP | 02200622 A | 8/1990 |
| JP | 3-11010 | 1/1991 |
| JP | 03014507 | 1/1991 |
| JP | 03014508 | 1/1991 |
| JP | 03112915 | 5/1991 |
| JP | 7002643 | 1/1995 |
| JP | 01228908 | 9/1998 |
| WO | 0381057 | 8/1990 |
| WO | WO 93/07903 | 4/1993 |
| WO | WO 94/02674 | 2/1994 |
| WO | WO 94/15580 | 7/1994 |
| WO | WO 95/03781 | 2/1995 |

OTHER PUBLICATIONS

Brody, "Chemical Peeling," St. Louis, Mosby Yearbook, p. 59–60, 1992.

Cabanes, et al., "Kojic Acid, a Cosmetic Skin Whitening Agent, is a Slow–Binding Inhibitor of Catecholase Activity of Tyrosinase," *J. Pharm. Pharmacol.*, 46:982–985, 1994.

Chiarello et al., "The TCA Masque: A New Cream Formulation Used Alone and in Combination with Jessner's Solution," *Dermatologic Surgery*, 22:687–690, 1996.

Cornell and Stoughton, "Correlation of the vasoconstriction assay and clinical activity in psoriasis," *Arch. Dermatology*, 121:63–67, 1985.

Ellis et al., "Superficial Micropeels: Glycolic Acid and Alpha–Hydroxy Acid with Kojic Acid," *Facial Plastic Surgery* 11(1): 15–21; 1995.

Garcia et al., "The Combination of Glycolic Acid and Hydroquinone or Kojic Acid for the Treatment of Melasma and Related Conditions," *Dermatologic Surgery* 22:443–447; 1996.

Horvath, "The Light Peel," *Bulletin of the Association of Military Dermatologists* 18:5; 1970.

Kligman, Cosmetics and the Skin, Wells & Lubowe, Reinhold, 1964.

Monheit, "The Jessner's + TCA peel: A Medium–Depth Chemical Peel," *Journal of Dermatologic Surgery and Oncology* 15(9): 945–960; 1989.

Rubin, "An Overview of Chemical Peeling," Plastic Surgery Products, Skin Care, pp. 14–15, Apr. 1995.

Rubin, "Manual of Chemical Peels: Superficial and Medium Depth". Philadelphia, J.B. Lippincott Company, 1995: 79–88.

Sulzberger, "Dermatologic Therapy," Chicago, Year Book Medical Publishers, 1940: 76–80.

Tse, "A Clinical and Histologic Evaluation of Two Medium–Depth Peels: Glycolic Acid Versus Jessner's Trichloroacetic Acid," *Dermatologic Surgery* 22:781–786; 1996.

Product Name: PCA Peel® with hydroquinone. Composition: 55% ethanol/water, 15% salicylic acid, 15% lactic acid, 10% citric acid, 3% kojic acid, and 2% hydroquinone. Estimated Date of Sale: Oct. 27, 1993.

Product Name: PCA Peel® without hydroquinone. Composition: 57% ethanol/water, 15% salicylic acid, 15% lactic acid, 10% citric acid, 3% kojic acid. Estimated Date of Sale: Nov. 1993.

Product Name: PCA Peel® with hydroquinone and resorcinol. Composition: 52% ethanol/water, 14% lactic acid, 14% salicylic acid, 3% kojic acid, 2% hydroquinone, and 1% citric acid. Estimated Date of Sale: May 1994.

\* cited by examiner

FIG. 1

FITZPATRICK CLASSIFICATION SYSTEM

| Skin Type | Skin Color | Characteristics |
|---|---|---|
| I | White | Always burns, never tans |
| II | White | Usually burns, tans less than average |
| III | White | Sometimes mild burn, tans about average |
| IV | White | Rarely burns, tans more than average |
| V | Brown | Rarely burns, tans profusely |
| VI | Black | Never burns, deeply pigmented |

*FIG. 2*

| GLOGAU CLASSIFICATION | | |
|---|---|---|
| Damage | Description | Characteristics |
| Type I (mild) | "No wrinkles" | Early photoaging<br>• mild pigmentary changes<br>• no keratoses<br>• minimal wrinkles<br>Patient age-20's or 30's<br>• minimal or no makeup<br>• minimal acne scarring |
| Type II (moderate) | "Wrinkles in motion" | Early to moderate photoaging<br>• early senile lentigines visible<br>• keratoses palpable but not visible<br>• parallel smile lines beginning to appear<br>Patient age-late 30's or 40's<br>• some foundation usually worn<br>• mild acne scarring |
| Type III (advanced) | "Wrinkles at rest" | Advanced photoaging<br>• obvious dyschromia, telangiectasias<br>• visible keratoses<br>• wrinkles present even when not moving<br>Patient age-50's or older<br>• heavier foundation always worn<br>• acne scarring present that makeup does not cover |
| Type IV (severe) | "Only wrinkles" | Severe photoaging<br>• yellow-gray skin color<br>• prior skin malignancies<br>• wrinkles throughout, no normal skin<br>Patient age-60's or 70's<br>• makeup cannot be worn-it cakes and cracks<br>• severe acne scarring |

HYDROXY-KOJIC ACID SKIN PEEL

This appln is a con of Ser. No. 09/299,788 Feb. 22, 1999 U.S. Pat. No. 6,300,369 which is a con of Ser. No. 08/795,231 Feb. 10, 1997 U.S. Pat. No. 5,874,463 which is a continuation-in-part of U.S. patent application Ser. No 08/328,006 filed Oct. 24, 1994, abn. The entire text of the above-referenced disclosures is specifically incorporated by reference herein without disclaimer.

BACKGROUND OF THE INVENTION

1. Field of the Invention

The present invention relates to skin peels utilizing alpha and beta hydroxy or keto acids as a topical treatment for hyperpigmentation, melasma, dyschromia, rhytides, photodamage and aging. Preferred peels contain alpha and beta hydroxy or keto acids with kojic acid or its derivatives in a dermatologically acceptable carrier such as an ethanoic/water mixture. Optionally, hydroquinone or its derivatives and other skin lighteners may also be employed in the peel when conditions warrant.

2. Description of Related Art

Skin peels are classified into three general types: light or superficial, medium and deep.

The deep peel utilizes phenol as a primary ingredient. Phenol ($C_6H_5OH$) obtained from coal tar and also called carbolic acid was first described as a peel in 1882 by the German dermatologist Dr. P. G. Unna. In 1903, Dr. G. M. Mackee, a British dermatologist began using phenol peels for acne scarring. Phenol peels were used as a treatment for gunpowder burns of the face in World War I. In the 1930s and 40s Antoinette la Gasse used phenol peels to improve scarring and wrinkles in a Los Angeles salon. Dr. J. C. Urkov described a phenol peel under occlusion as a method for wrinkle treatment in 1946. In the 1960s, Dr. Adolph Brown, a maxillofacial surgeon, and his wife, Dr. Martha Brown, a dermatologist, performed detailed studies on phenol peel formulas and toxicities that resulted in a renaissance in phenol peeling. Dr. F. C. Combes and Dr. P. A. Sperber devoted considerable effort to developing a buffered phenol peel that would be less caustic than the extremely harsh full strength phenol peels. Also in the early 1960s, Dr. Thomas M. Baker collaborated with Dr. H. L. Gordon to develop a saponated phenol peel that is still in use today.

Phenol peels penetrate as far as the mid-reticular dermis and cause virtually complete necrosis of the epidermis and the papillary dermis that extends into the reticular dermis. Phenol is directly toxic to the myocardium and cardiac arrhythmias have been reported with many phenol peels. If a high dose is used they are also hepatotoxic and nephrotoxic. Certain predisposed individuals may experience idiosyncratic cardiac death from an adrenalin release due to facial pain transmitted from the trigeminal nerve to the cardiac vagal nerve or from the cerebral cortex directly to the cardiac sinoatrial node. The possibility of complications from the aforementioned deep phenol peels is significant. Hypertrophic, atrophic and keloidal scarring were reported by 21% of 588 plastic surgeons surveyed in a 1981 report in the journal of *Plastic and Reconstructive Surgery*. Other possible complications of the phenol peels include adverse textural changes to the phenol peeled skin and infectious conditions such as bacterial pyoderma, toxic shock syndrome, herpes simplex virus, and Epstein-Barr virus keratitis. Unsightly pigmentary occurrences that may result from the said phenol peels include hyperpigmentation, hypopigmentation, porcelain depigmentation, visible lines of demarcation with unpeeled skin and nevi accentuation.

Phenol peels are outside the realm of utilization of the present invention and from the aforegoing description of the possible adverse results elicited by the use of the said phenol peels it should be readily apparent that safe, efficacious peels such as the present invention have great utility in dermatologic practice.

Medium depth peels are defined as those that penetrate to the upper reticular dermis. The most commonly used medium depth peel is the 40% to 60% trichloroacetic acid peel. The German dermatologist, Dr. P. G. Unna, first employed trichloroacetic acid as a peeling agent and described his technique in 1882. Dr. S. Monash conducted experiments with trichloroacetic acid peeling and published a paper entitled "The uses of diluted trichloroacetic acid in dermatology" in 1945. Dr. S. Ayres combined the trichloroacetic acid peel teachings of Dr. S. Monash with his own conclusions based on clinical experience and published two papers relating to trichloroacetic acid peeling in the early 1960s. Dr. S. S. Resnik, Dr. L. A. Lewis and Dr. B. H. Cohen published the paper "Trichloroacetic acid peeling" in the journal *Cutis* in 1976. Dr. S. J. Stegman's histologic findings with trichloroacetic acid peeling in the early 1980s began efforts to investigate skin peeling in a controlled and scientific manner. Dr. Harold J. Brody and Dr. C. W. Hailey published "Medium depth peeling of the skin" in the *Journal of Dermatologic Surgery and Oncology* in 1986. Dr. Gary Monheit pioneered combination peels by combining the trichloroacetic acid peel with the superficial peel utilizing Dr. Jessner's solution and published "The Jessner's+TCA peel" in the *Journal of Dermatologic Surgery and Oncology* in 1989. The most recent developments in trichloroacetic acid peeling are found in the "Manual of Chemical Peels: Superficial and Medium Depth" by Dr. Mark G. Rubin. U.S. Pat. Nos. 4,874,361 and 5,166,176 issued to Dr. Zein E. Obagi and Dr. George H. Michel describe the use of trichloroacetic acid peels in combination with surfactants, humectant-emollients and emulsifiers for healing damaged skin.

Medium depth peeling with trichloroacetic acid does not require hospital care and general anesthesia as the phenol deep peels do, nor is there near the number of possible complications and adverse results, however, there is a significant risk of scarring at high concentrations of trichloroacetic acid. The present invention is quite suitable as a pretreatment for the trichloroacetic acid peels and may reduce the concentration requirements while still obtaining comparable results.

Superficial peels, as in the case of medium and deep peels, were pioneered by the German dermatologist, Dr. P. G. Unna, and the use of salicylic acid and resorcinol as superficial peeling agents were described by Dr. Unna in 1882. In the 1930s a superficial peel containing resorcinol, salicylic acid, lactic acid, oil of rose and ethyl hydrate was utilized and this peel was reported by Dr. J. J. Eller and Dr. S. Wolff in their article "Skin Peeling and Scarification" in the *Journal of the American Medical Association* in 1941. A superficial peel comprised of resorcinol, salicylic acid, and lactic acid was reported on by Dr. F. C. Combes, Dr. P. A. Sperber and Dr. M. Reisch. Essentially the same superficial peel was commented on in the paper "The light peel" in the *Bulletin of the Association of Military Dermatologists* by Dr. P. N. Horvath in 1970. The prominent dermatologist, Dr. Max Jessner, extensively applied this same superficial peel on many patients to the extent that to the current time this superficial peel is known to over 40,000 United States dermatologist as the Jessner's solution and as the Combes' Peel or Horvath's Concoction. Prior art contains U.S. Pat.

No. 4,608,370 issued to Richard B. Aronsohn, a California dermatologist relating to a skin formulation which is in essence merely a diluted version of the superficial peel described in the literature. The present invention in its various embodiments successfully replaces the Jessner's Solution, Combes' Peel and Horvath's Concoction used by United States dermatologists for the last 60 years because of the present invention's improved biocompatability, higher efficacy and wider versatility over the range of skin complaints exhibited to the dermatological practitioners.

Superficial peels range in depth from the stratum granulosum to the upper papillary dermis depending on formulation, technique and patient skin type. Complications with superficial peels are few and mild if experienced. Weekly or monthly superficial peels may be performed to achieve results more comparable with the deeper peels.

None of the prior art, to applicant's knowledge, discloses a superficial peel utilizing alpha and beta hydroxy or keto acids with kojic acid or its derivatives to treat photodamage, rhytides and pigmentary dyschromias.

Further, prior art relating to therapeutic skin peeling does not disclose use of citric acid, a major component of the Kreb's cycle, tricarboxylic acid cycle or citric acid cycle as it is variously referred to in mammalian metabolism.

Whereas prior art does not contain disclosure of the fungal metabolite kojic acid or its derivatives widely known as skin lighteners in any skin peel of any depth their utilization as skin peel components may be considered novel.

An object of the invention in its various embodiments is to provide the practicing dermatologist with an array of superficial peels capable of addressing a wide variety of functional and cosmetical skin defects as might be encountered in everyday practice without significant irritation or complication.

It is another object of this invention to provide a safe and efficient peel in the treatment of regional hyperpigmentation caused by melanocytic hyperactivity, such as idiopathic melasma occurring during pregnancy or melasmas secondary to estrogen-progesterone contraception. The peels of the present invention are also effective for localized hyperpigmentation and benign melanocytic proliferations, such as senile pigmentary spots, actinic photosensitization and post-lesion scarring.

It is still another object of this invention to provide a selection of peels beneficial in the treatment and prevention of acne.

SUMMARY OF THE INVENTION

The present invention relates to alpha and beta hydroxy or keto acid skin peels with kojic acid or derivatives thereof in an ethanol/water carrier. Skin peels of the present invention utilizing alpha and beta hydroxy or keto acids with kojic acid induce beneficial biomolecular events in the skin such as stratum corneum separation in sheetlike fragments due to reduced corneocyte cohesion. This sheetlike separation is histologically found to occur at the innermost level of the stratum corneum just above the stratum granulosum, resulting in a beneficial thinning of the stratum corneum. In aged skin the thickness of the stratum corneum may reach as high as 70 to 80 cells thick due to lowered activity of certain desquamatory regulating enzymes. Periodic therapeutic skin peels with the present invention will result in a stratum corneum that is more resilient with a thickness of 16 to 20 cells thick which is more typical of 20 year old skin. Stratum corneums rebuilt utilizing the therapeutic skin peels of the present invention will exhibit improved barrier function due to increased levels of ceramides produced by keratinocytes. The stratum corneum barrier is largely dictated by extracellular lipids consisting of a mixture of ceramides, cholesterol and fatty acids together with smaller amounts of cholesterol sulphate, glucosyl ceramides and phospholipids. In addition to their pivotal role in barrier function, these lipids are also important for the desquamatory and mechanical properties of the stratum corneum. The levels of stratum corneum lipids, especially ceramides and their subtypes, are optimized by the correct selection of the most appropriate skin peel based on the Fitzpatrick skin type classification, Glogau photodamage classification system and whether the patient has a desquamatory disorder or other skin condition. Stratum corneum rebuilding allows the atrophic epidermis caused by intrinsic and extrinsic aging to regain normal or near-normal thickness and appearance. Dermal alterations due to application of the preferred embodiment of the present invention include increased accumulation of dermal glycosaminoglycans, including hyaluronic acid. Accelerated formation of collagen will ensue with periodic application of the present invention. Clinically visible increased plumpness of the skin will occur in most patients, resulting in a more attractive, youthful appearance.

In another embodiment, the present invention involves a topical skin exfoliation composition comprising lactic acid, kojic acid, citric acid and salicylic acid. It may further comprise hydroquinone. In one embodiment, the composition is 16–14 parts L+lactic acid, 18–24 parts citric acid, 2 parts kojic acid and 50 to 65 parts ethyl alcohol. A preferred topical skin exfoliation composition useful in skin peels involves 10–16 parts L+lactic acid, 12–18 parts citric acid, 14 parts salicylic acid, 2 parts kojic acid and 50 to 65 parts ethyl alcohol.

Included in the present invention in one embodiment is a method for facial exfoliation comprising:

a) obtaining a composition comprising lactic acid, kojic acid, citric acid and salicylic acid;

b) applying a coating of said composition to the facial skin in an amount effective to cause skin peeling.

This method may further comprise additional steps as follows:

a) prior to applying said composition, thoroughly cleansing facial skin to be exfoliated using an appropriate degreaser;

b) applying a second coat of said composition to the facial skin 2 to 4 minutes after the first coat;

c) applying third and further coats of said composition to the facial skin at 2 to 4 minute intervals until appearance of crystals or "frosting";

d) cleaning the facial skin with a water dampened sponge or equivalent;

e) applying hydrator mixture comprising octylmethoxy cinnaminate, benzophenone 3 and titanium dioxide in aloe vera solution the first night after peel; and f) performing additional treatments at biweekly or monthly intervals until desired results are obtained.

None before have prepared a composition according to the present invention for the use of a superior skin exfoliation or peeling composition. Of course, neither has such composition been used in a method for such a procedure.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Lactic acid $CH_1CHOHCOOH$ (2-hydroxypropanoic acid), owing to the nonsymmetric nature of the molecule is known to exist in D.L. and DL forms. DL-lactic acid, also known as ordinary lactic acid, occurs in sour milk and is produced by the action of lactic acid bacteria. L-lactic acid is the form that occurs in the blood of man and animals (5–40 mg/100 ml). The skin content of L-lactic acid is approximately three times higher than that of the blood. Lactic acid concentration often increases in blood and muscle after vigorous exercise. L-lactic acid is also present in liver, kidney, thymus gland, human amniotic fluid, and other organs and body fluids. Biochemically, lactic acid is one of the key substances in carbohydrate metabolism. Because application of D-lactic acid does not increase stratum corneum ceramide levels, the present invention utilizes the L-lactic isomer in the preferred embodiments. Lactic acid is nontoxic.

Glycolic acid has the smallest molecule of the alpha hydroxy acids allowing for enhanced penetration into the dermal layers when conditions warrant. It is commercially available as a white crystalline compound that is 99% pure and also as a 70% aqueous solution. Preferred embodiments include addition of kojic acid and derivatives thereof along with additional components such as hydroquinone in the 1 to 2% range. Skin response to glycolic acid depends not only on its concentration and pH but also on other factors such as the amount of free acid delivered to the skin, the duration of contact, preparation of the skin before peeling, and the condition of the skin before treatment.

Citric acid is a tricarboxylic acid with one hydroxyl group at the alpha position to one carboxyl group; at the same time the hydroxyl group is also at the beta position to the two remaining carboxyl groups. Therefore citric acid may be called an alpha hydroxy acid or a beta hydroxy acid, depending on which carboxyl group is referred to. Citric acid is present as a carbohydrate metabolite in the skin. Citric acid inhibits the activity of phosphofructokinase in glycolysis, which may lead to enhanced glucuronate production and increased biosynthesis of mucopolysaccharides that serve as the intercellular cementing substance for normal keratinization of the epidermis. A surprisingly dramatic synergism has been discovered in preferred embodiments of the present invention that utilize L-lactic acid and citric acid perhaps because of the powerful antioxidant properties of citric acid. Citric acid is nontoxic.

Ascorbic acid is a lactone form of 3-keto-2,4,5,6-tetrahydroxyhexanoic acid, which is both an alpha hydroxy acid and a beta keto acid. L-ascorbic acid is both a regulator and stimulator of collagen synthesis and plays a vital role in the performance of the peel in several preferred embodiments of the present invention because of the potent antioxidant and skin lightening effect.

Saliclyic acid (ortho-hydroxybenzoic acid) has been a mainstay in dermatologic therapy for many decades. In the present invention salicylic acid serves as a keratolytic and exhibits synergism with alpha hydroxy acids as a penetration enhancer in some peels.

Pyruvic acid is a alpha keto acid that is chemically related to lactic acid in that the hydroxyl group can be replaced by a keto group at the alpha position of the acid. Pyruvic acid is present as a carbohydrate metabolite in the skin and is converted to lactic acid by a lactate dehydrogenase enzyme during carbohydrate metabolism.

Tartaric acid is an alpha hydroxy that is a dicarboxylic acid with two hydroxyl groups at the alpha positions of the acid, similar to the compound formed from two molecules of glycolic acid. Tartaric acid is nontoxic and occurs as a carbohydrate metabolite in the skin.

Kojic acid (5-hydroxy-w-(hydroxymethyl)-4-gamma-pyrone) is employed in the present invention to chelate to the copper atoms in tyrosinase, the key enzyme in melanin production. Kojic acid is a fungal metabolite that has been known to display contact dermatitis potential only with prolonged daily use.

Malic acid is a dicarboxylic acid with one hydroxyl group at the alpha position of the acid, similar to the compound formed from one molecule of glycolic acid and one molecule of acetic acid. Malic acid is nontoxic and is present as a carbohydrate metabolite in the skin. Certain embodiments of the present invention utilize malic acid to increase mucopolysaccaride production.

Hydroquinone, hydroquinone monobenzyl ether, and hydroquinone monethyl ether act as substitute substrate for the melanization enzyme tyrosinase and may be included in certain peels to enhance the skin lightening ability of said peel. The addition of citric acid and malic acid in peeling containing hydroquinone or its derivatives serve to act as antioxidants to help stabilize the hydroquinone in the peel and to enhance the penetration and the efficacy of hydroquinone.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

The following is a general procedure or method for application of the selected superficial or intermediate peels of the present invention which may be applied on a periodic basis:

a. thorough cleansing of facial skin to be peeled using an appropriate degreaser such as alcohol, acetone, freon or chlorhexidine. Since this is meant to be a superficial type of peel, there is no need to do an aggressive scrub to clean the skin. The goal is to degrease the skin, not to strip off any remaining stratum corneum.

b. apply light coating of the selected peel (as formulated in the following examples) using a synthetic fiber fan brush or equivalent, starting at the chin and working upwards with particularly thorough coverage of hyperpigmented areas;

c. apply second coat after 2 to 4 minutes;
d. apply third and further coats at 2 to 4 minute intervals until appearance of crystals or "frosting";
e. after appearance of crystals or "frosting", clean face with distilled water dampened sponge;
f. apply hydrator mixture with ingredients such as octylmethoxy cinnaminate, benzophenone 3 and Litanium dioxide in aloe vera solution the first night after peel;
g. perform additional treatments at biweekly or monthly intervals until desired results are obtained;
h. avoid sun exposure and apply sunblocking agent if exposure is necessary.

A light or superficial peel is performed essentially as outlined for the intermediate peel except one or two coats only of the peel are applied instead of applying coats until visible crystal production or "frosting."

EXAMPLE 2

A therapeutic and prophylactic superficial peel in solution form may be prepared as follows:

L-lactic acid 14 grams, citric acid 14 grams, salicylic acid 14 grams, and kojic acid 2 grams are dissolved in a mixture of ethanol 40 ml and distilled water 16 ml. and stirred until a clear solution is obtained. The solution should be tightly capped until used.

EXAMPLE 3

Another therapeutic and prophylactic peel with the addition of the skin lightener hydroquinone may be prepared as follows:

L-lactic acid 14 grams, citric acid 14 grams, salicylic acid 14 grams, kojic acid 2 grams, and hydroquinone 1 gram are dissolved in a mixture of ethanol 39 ml and distilled water 16 ml. and stirred until a clear solution is obtained. This formulation is appropriate for age spots and keratoses.

EXAMPLE 4

A peel suitable for more than superficial peeling with superior lightening capability may be prepared as follows:

Glycolic acid 70 grams and kojic acid 2 grams are dissolved in 24 ml distilled water and 4 ml ethanol.

EXAMPLE 5

A superficial peel with enhanced antioxidant and skin lightening properties may be prepared as follows:

L-lactic acid 14 grams, citric acid 14 grams, salicylic acid 14 grams, kojic acid 2 grams, and ascorbic acid 2 grams are dissolved in 38 ml ethanol and 26 ml distilled water until a clear solution is obtained.

EXAMPLE 6

The effect of the skin peeling treatment with and without hydroquinone was tested by comparative application of the method. In this example the subjects were directed to wash both arms with cleanser, consisting of acetone. The arms were then cleaned with a balancing toner. Then, four successive coats of the skin peeling composition, consisting of Example 3 were applied. Subjects were then directed to wipe off the dried film with more toner and to apply sunscreen to protect the treated skin. This was followed by a twice-daily regiment of wash, toner, and sunscreen.

Figure 1:
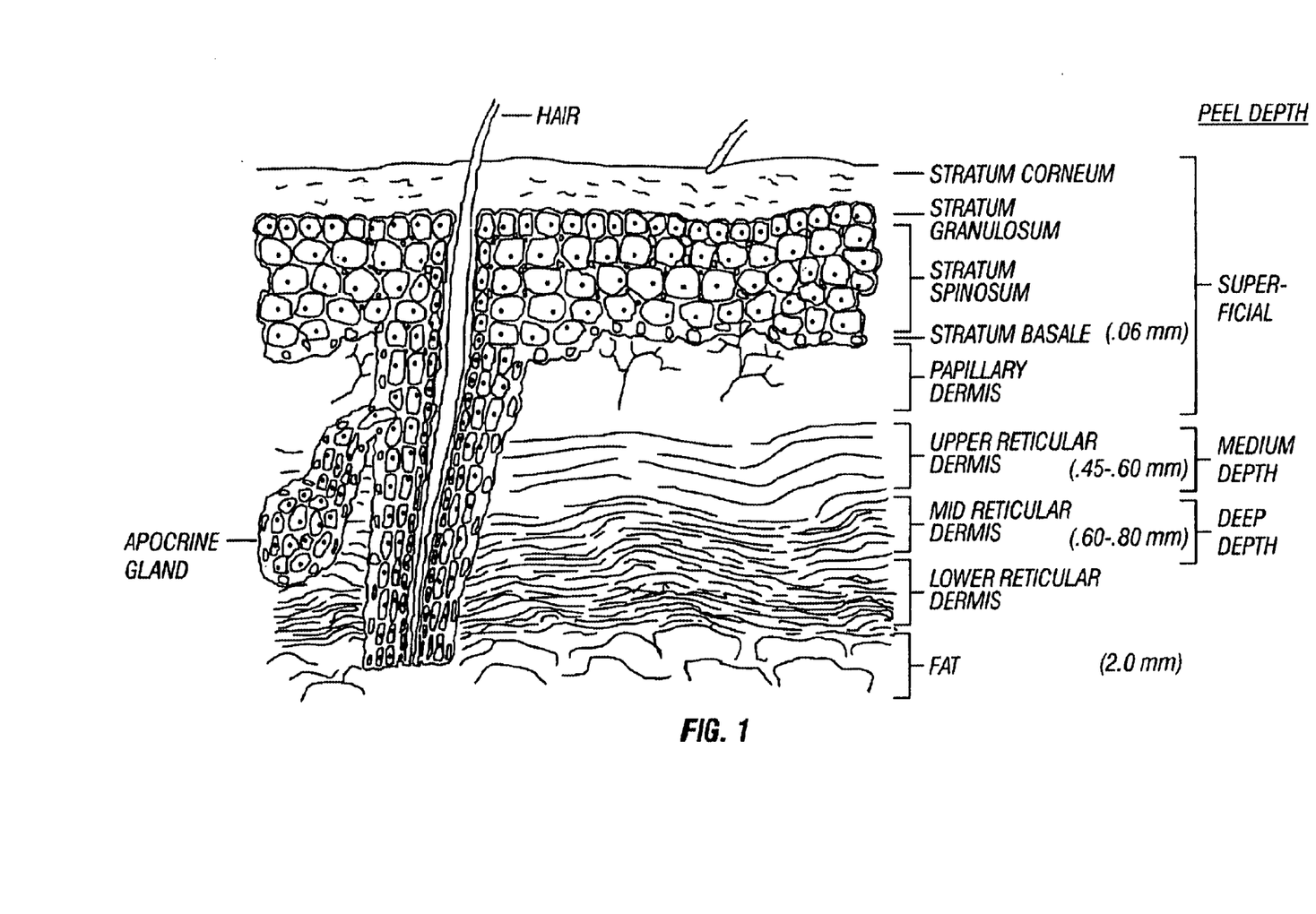
FIG. 1. Peel depth drawing.
Figure 2:
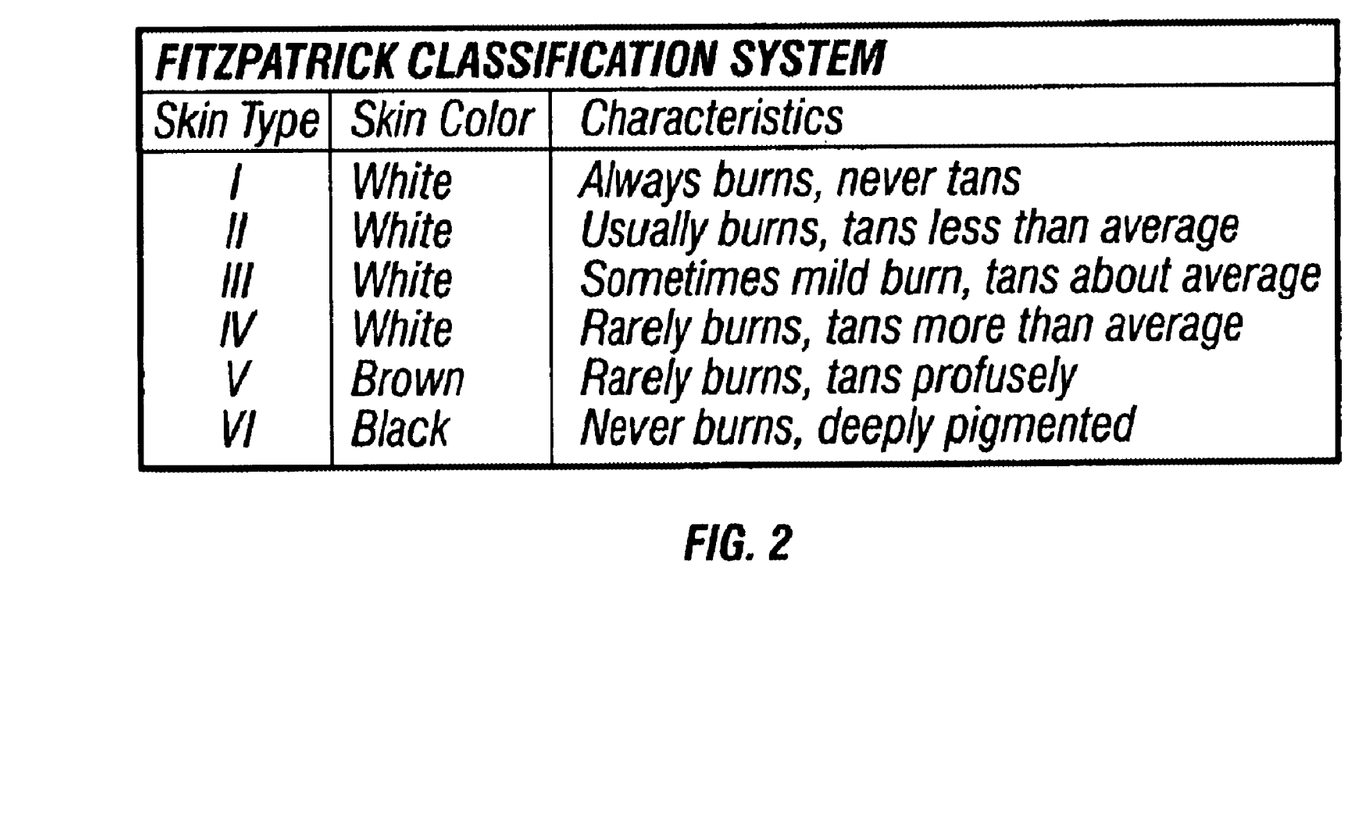
FIG. 2. Fitzpatrick skin type chart.
Figure 3:
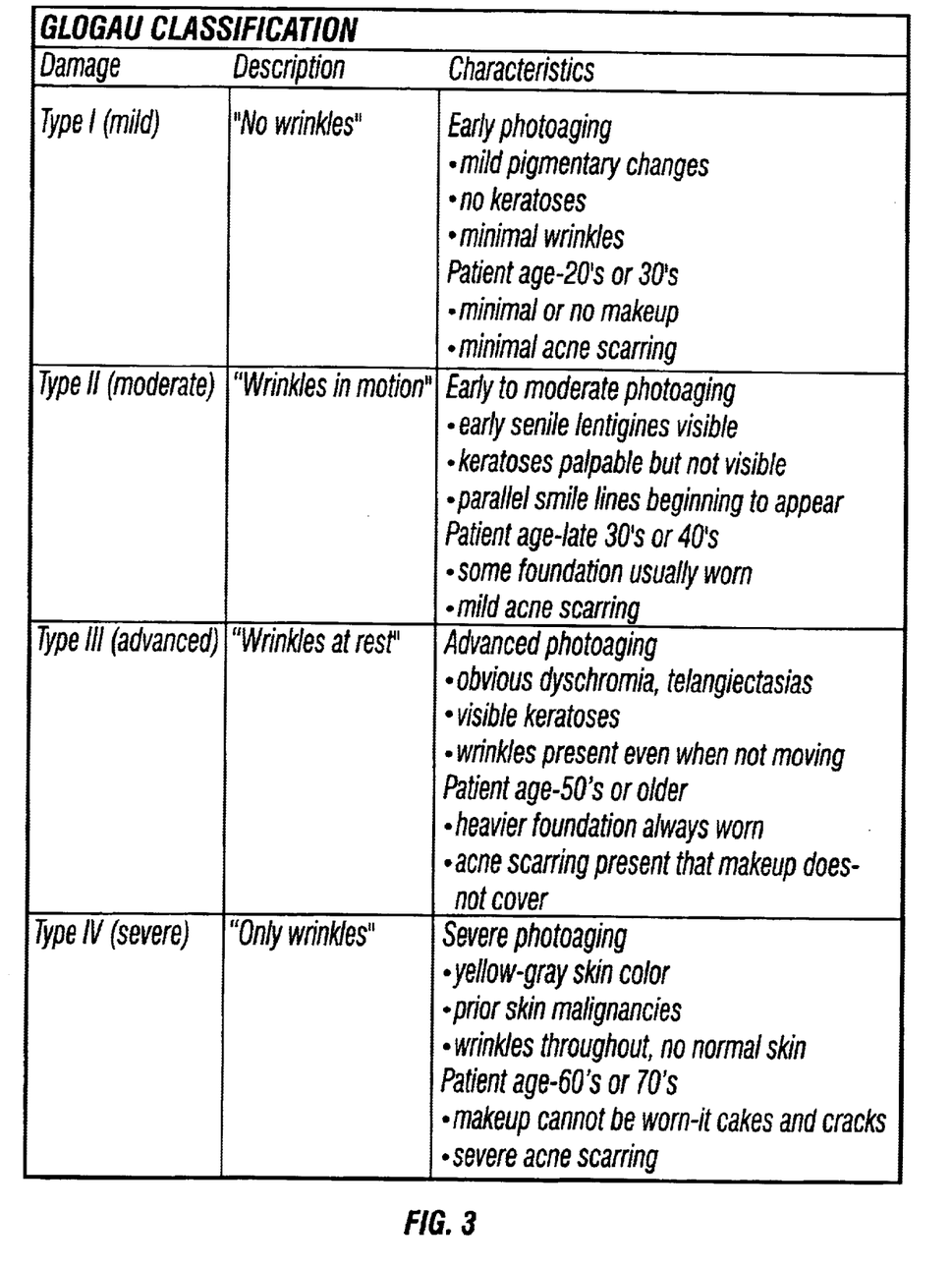
FIG. 3. Glogau photodamage chart.
Figure 4A:
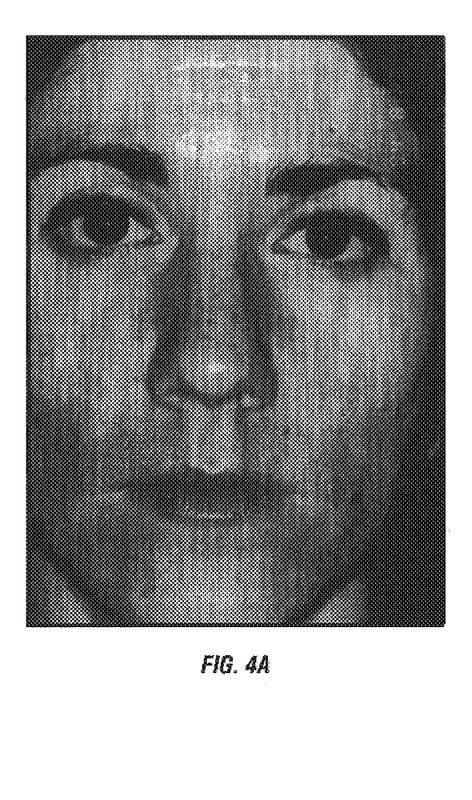
FIG. 4. Patient treated with skin peel shows marked improvement in skin appearance.
Figure 4B:
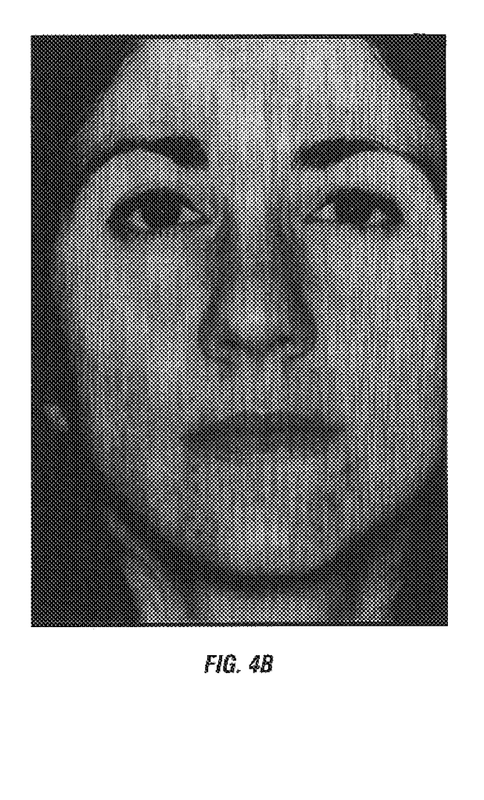
Figure 5A:
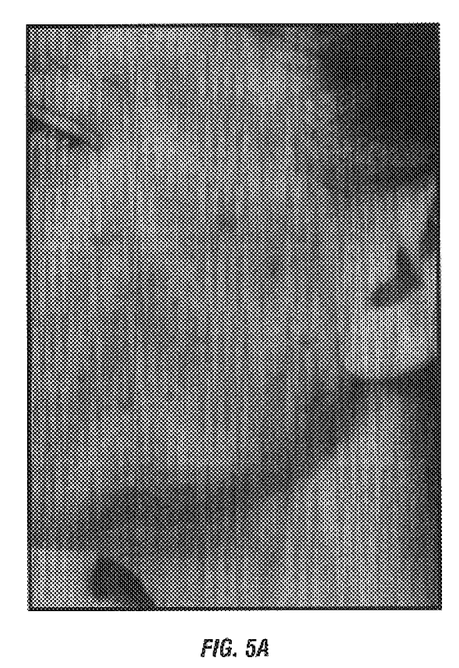
FIG. 5. Patient treated with skin peel shows marked improvement in acne symptoms.
Figure 5B:
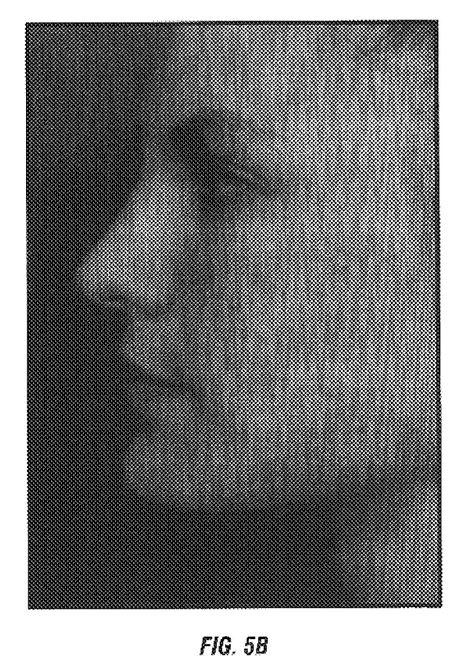
Figure 5C:
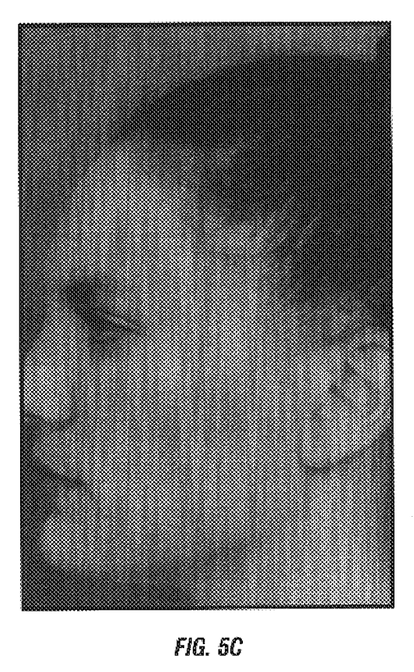
Figure 5D:
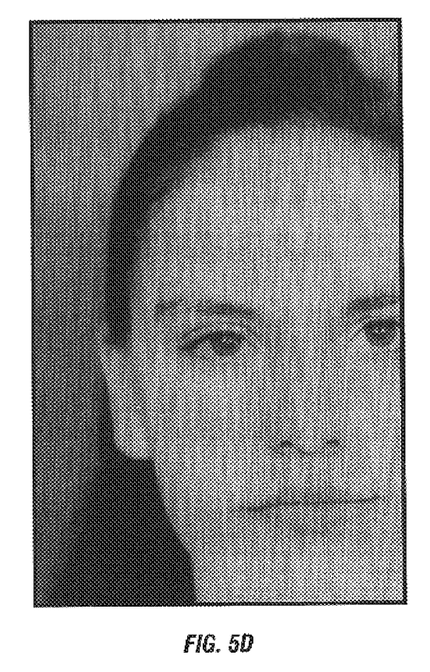

The subjective improvement each patient saw in their own arm appearance averaged 28% in the arm treated without hydroquinone and 64% in the arm treated with hydroquinone. When compared with Jessner's solution, the most commonly used light peeling agent, the present formulation achieved significantly improved results. The effectiveness of the skin peeling treatment on skin lightening and acne reduction are shown in the enclosed FIGS. 4 and 5.

Based on the information given in this detailed description of the invention, it is readily a apparent that the invention provides an excellent skin rejuvenating modality consisting primarily of an array of predominantly physiologic components, which when precisely combined have a profound synergistic beneficial effect upon application to aged, photodamaged, hyperpigmented, and acne troubled skin. In essence, the present invention accelerates, augments, and enhances the facial skin's inherent repair and maintenance mechanisms.

Since special individual skin conditions may warrant changes and modifications of the present invention and can be made readily by those skilled in the art without departing from the basic concept of the present invention, the present invention shall not be limited except by the scope of the appended claims.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

References

The following references, to the extent that they provide exemplary procedural or other details supplementary to those set forth herein, are specifically incorporated herein by reference.

U.S. Pat. No. 5,520,918, May 1996 to Smith.
U.S. Pat. No. 5,505,948, April 1996 to Rapaport.
U.S. Pat. No. 5,166,176, November 1992 to Obagi.
U.S. Pat. No. 4,874,361, October 1989 to Obagi.
U.S. Pat. No. 4,608,370, August 1986 to Aronsohn.

Other Publications

Andrews, G. "Diseases of the Skin", Philadelphia, W B Saunders, 1928:240–248.
Chiarello, Stephen E.; Resnik, Barry I.; and Resnik Sorrell S.: The TCA Masque: A New Cream Formulation Used Alone and in Combination with Jessner's Solution. *Dermatologic Surgery* 22:687–690; 1996.
Brody, Harold J., "Chemical Peeling", St. Louis, Mosby Year Book, 1992:59–60.
Ellis, David A. F.; Tan, Andre K. W.; and Ellis, Craig S.: Superficial Micropeels: Glycolic Acid and Alpha-Hydroxy Acid with Kojic Acid. *Facial Plastic Surgery* 11(1): 15–21; 1995.
Garcia, Alicia; and Fulton, James E., Jr.: The Combination of Glycolic Acid and Hydroquinone or Kojic Acid for the Treatment of Melasma and Related Conditions. *Dermatologic Surgery* 22: 443–447; 1996.
Horvath, Peter N.: The Light Peel. *Bulletin of the Association of Military Dermatologists* 18:5; 1970.

Monheit, Gary: The Jessner's + TCA peel: A Medium-Depth Chemical Peel. *Journal of Dermatologic Surgery and Oncology* 15(9): 945–960; 1989.

Rubin, Mark G.: "Manual of Chemical Peels: Superficial and Medium Depth". Philadelphia, J. B. Lippincott Company, 1995: 79–88.

Sulzberger, Marion. "Dermatologic Therapy". Chicago, Year Book Medical Publishers, 1940: 76–80.

Tse, Yardy; Ostad, Ariel; Lee Hyun-Soo; Levine, Vicki J.; Koenig, Karen; Kamino, Hideko; and Ashinoff, Robin. A Clinical and Histologic Evaluation of Two Medium-Depth Peels: Glycolic Acid Versus Jessner's Trichloroacetic Acid. *Dermatologic Surgery* 22:781–786; 1996.

What is claimed is:

1. A skin peel composition comprising a mixture of:
   a skin exfoliation agent; and
   kojic acid,
   wherein said kojic acid comprises up to 15% of said composition,
   and wherein said composition induces a patient's skin to peel when one or two coats are applied to the patient's skin for two to four minutes.

2. The skin peel composition of claim 1 wherein said skin exfoliation agent comprises 10% to 20% salicylic acid.

3. The skin peel composition of claim 2 further comprising lactic acid.

4. The skin peel composition of claim 3 wherein said composition comprises 10% to 20% lactic acid.

5. The skin peel composition of claim 1 further comprising citric acid, and wherein said citric acid comprises up to 20% of said composition.

6. The skin peel composition of claim 2 wherein said composition comprises 10% to 20% lactic acid and up to 15% citric acid.

7. The skin peel composition of claim 1 further comprising a water-ethanol mixture.

8. The skin peel composition of claim 7, wherein said composition comprises a 45% to 80% water-ethanol mixture.

9. The skin peel composition of claim 8 wherein said water-ethanol mixture has 70 parts water and 30 parts ethanol.

10. The skin peel composition of claim 1 wherein said kojic acid comprises up to 5% of said composition and said skin exfoliation agent is selected from the group consisting of glycolic acid, pyruvic acid, retinoic acid, resorcinol, tartaric acid, malic acid, and salicylic acid.

11. The skin peel composition of claim 10 wherein said skin exfoliation agent comprises 5% to 20% salicylic acid and up to 5% retinoic acid.

12. The skin peel composition of claim 10 further comprising 5% to 15% aloe vera.

13. The skin peel composition of claim 10 further comprising a water-ethanol mixture.

14. The skin peel composition of claim 13, wherein said composition comprises a 15% to 80% water-ethanol mixture.

15. The skin peel composition of claim 14 wherein said water-ethanol mixture has 70 parts water and 30 parts ethanol.

16. The skin peel composition of claim 1 wherein said skin exfoliation agent comprises 5% to 20% salicylic acid and up to 5% resorcinol.

17. The skin peel composition of claim 1 wherein said kojic acid comprises up to 5% of said composition and said composition further comprises hydroquinone, said hydroquinone comprising up to 2% of said composition.

18. The skin peel composition of claim 16 further comprising 5% to 20% citric acid.

19. The skin peel composition of claim 17 further comprising 5% to 20% citric acid and 5% to 15% casein.

20. The skin peel composition of claim 19 further comprising a water-ethanol mixture.

21. The skin peel composition of claim 20 wherein said composition comprises a 15% to 80% water-ethanol mixture.

22. The skin peel composition of claim 21 wherein said water-ethanol mixture has 70 parts water and 30 parts ethanol.

23. The skin peel composition according to claim 1 further comprising 0.2% to 6% hydroquinone.

24. The skin peel composition according to claim 23 wherein said composition comprises 0.2% to 2% hydroquinone.

25. The skin peel composition of claim 16 further comprising 5% to 20% citric acid.

26. The skin peel composition of claim 23 further comprising 5% to 20% citric acid and 5% to 15% casein.

27. The skin peel composition of claim 1 wherein said skin exfoliation agent comprises 14% salicylic acid, and said kojic acid comprises 3% of said composition.

28. The skin peel composition of claim 27 further comprising citric acid.

29. The skin peel composition of claim 28 comprising 10% citric acid.

30. The skin peel composition of claim 27 further comprising lactic acid.

31. The skin peel composition of claim 30 comprising 14% lactic acid.

32. The skin peel composition of claim 31 further comprising 10% citric acid.

33. The skin peel composition of claim 31 further comprising a water-ethanol mixture.

34. The skin peel composition of claim 33 comprising a 59% water-ethanol mixture, and wherein said water-ethanol mixture has 70 parts water and 30 parts ethanol.

35. The skin peel composition of claim 1 wherein said kojic acid comprises between 1% to 5% of said composition, and said skin exfoliation agent comprises 10% to 20% salicylic acid of said composition, and said composition further comprises 5% to 15% citric acid and 10% to 20% lactic acid.

36. The skin peel composition of claim 35 further comprising 0.1% to 3% hydroquinone.

37. The skin peel composition of claim 36 further comprising 45% to 80% aloe vera.

38. A skin peel composition comprising 10% to 20% lactic acid, 5% to 15% citric acid, 1% to 5% kojic acid, and 45% to 80% ethanol-water mixture.

39. The skin peel composition according to claim 38 further comprising 0.1% to 3% hydroquinone.

40. The skin peel composition according to claim 38 further comprising 0.2% to 6% hydroquinone.

41. The skin peel composition according to claim 40 wherein said composition comprises 0.2% to 2% hydroquinone.

42. The skin peel composition of claim 38 wherein said water-ethanol mixture has 70 parts water and 30 parts ethanol.

43. The skin peel composition of claim 1 further comprising either an ascorbate or glycyrrhizic acid.

44. The skin peel composition of claim 1 further comprising arbutin.

45. The skin peel composition of claim 43 further comprising hydroquinone.

46. A skin peel composition comprising salicylic acid, lactic acid, and a melanin bleaching agent, said melanin bleaching agent comprising citric acid,
   wherein said composition induces a patient's skin to peel when one or two coats are applied to the patient's skin for two to four minutes.

47. The skin peel composition of claim 46 comprising 5% to 20% citric acid.

48. The skin peel composition of claim 47 comprising 5 to 15% citric acid.

49. The skin peel composition of claim 46 comprising 10% citric acid.

50. A skin peel composition comprising a mixture of:
   a skin exfoliation agent;
   a skin penetrating agent;
   a melanin bleaching agent; and
   a melanin formation inhibiting agent selected from the group consisting of one or more of arbutin, ascorbic acid phosphate magnesium salt, L-ascorbates and kudzu roots, ascorbates and urea, alkylsalicylic acid, arginine, buthionine sulfoximine, benzophenone, caffeic acid, chitosans, chromone derivatives, cinnamic acid, citric acid, conchiolin hydrolyzate, cystamine, 5,6-dihydroxyindole, dicaffeoylquinic acid, ellagic acid, erthorbic acid glucoside, Feldamycin, ferulic acid, fuzi acid derived from aconitum root, gamma-L-glutamyl-L cystine, gamma-L-cystine disulfide, glucosamine, glycyrrhizic acid, glycyrrhetinic acid, gromwell seed extract, hydantoin, hydroquinone, hydroquinone glycoside, indomethicin methacin, kojic acid, kojic acid dimer, kojic acid glycosides, kojic acid succinimide ester, S-lactoyl glutathione, lavanols, licorice root extracts, linoleic acid, logwood extract, lysine and/or its derivatives, magnesium ascorbate, melanostatin, niacinimide, oxidized glutathione, phenylthiourea, phenol in low concentrations, f-polylysine, polyphenols, propionic acid, sulphur, superoxide dismutase, thiazoles, tranexamic acid, tricaffeoylquinic acid, vitamin K groups, and
   wherein said skin exfoliation agent is present in sufficient amounts to induce a patient's skin to undergo peeling when said composition is applied to the patient's skin.

51. The skin peel composition of claim 50 wherein said melanin bleaching agent is selected from the group consisting of citric acid, kojic acid, ascorbic acid, arbutin, hydroquinone, monobenzyl ether of hydroquinone, and monoethyl ether of hydroquinone, superoxide dismutase, gromwell seed extract, azelaic acid, mercaptopyridine, and glabridin.

52. The skin peel composition of claim 50 wherein said exfoliating agent is selected from the group consisting of glycolic acid, pyruvic acid, retinoic acid, resorcinol, tartaric acid, malic acid, and salicylic acid.

53. The skin peel composition of claim 50 wherein said skin penetrating agent is selected from the group consisting of crystal urea, aloe vera, casein, lactic acid, and alpha hydroxy acid mixtures.

54. The skin peel composition of claim 50 wherein said melanin bleaching agent also acts as a melanin formation inhibiting agent.

55. The skin peel composition of claim 50 wherein said melanin formation inhibiting agent is selected from the group consisting of kojic acid and hydroquinone, and wherein said melanin bleaching agent is selected from the group consisting of kojic acid and hydroquinone.

56. The skin peel composition of claim 55 wherein said skin penetrating agent comprises a mixture of alpha hydroxy acids.

57. The skin peel composition of claim 50 wherein said melanin formation inhibiting agent is selected from the group consisting of kojic acid and arbutin and said skin bleaching agent comprises kojic acid.

58. The skin peel composition of claim 57 further comprising citric acid.

59. The skin peel composition of claim 50 wherein said melanin formation inhibiting agent is selected from the group consisting of kojic acid or citric acid and said skin bleaching agent is selected from the group consisting of kojic acid and hydroquinone.

60. A skin peel composition comprising a mixture of:
   a skin exfoliation agent;
   a melanin formation inhibiting agent comprising glycyrrhizic acid;
   and wherein said composition induces a patient's skin to undergo light or intermediate peeling when one or two coats are applied to the patient's skin.

61. The skin peel of claim 56 further comprising a either lactic acid or glycolic acid.

62. The skin peel composition of claim 60 wherein said skin exfoliation agent is selected from the group consisting of salicylic acid, lactic acid, and glycolic acid.

63. The skin peel composition of claim 60 wherein said skin exfoliation agent comprises salicylic acid.

64. The skin peel composition of claim 63 wherein said composition comprises 10-20% salicylic acid.

65. The skin peel composition of claim 60 wherein said skin exfoliation agent comprises glycolic acid.

66. A skin peel composition comprising a mixture of:
   a skin exfoliation agent;
   at least one melanin formation inhibiting agent selected from the group consisting of kojic acid, L-ascorbate, licorice root extract, hydroquinone, arbutin, and superoxide dismutase;
   and wherein said composition induces a patient's skin to undergo light or intermediate peeling when one or two coats are applied to the patient's skin for two to four minutes.

67. The skin peel composition of claim 66 wherein said at least one melanin inhibiting agent comprises L-ascorbate.

68. The skin peel composition of claim 66 wherein said at least one melanin inhibiting agent comprises licorice root extract.

69. The skin peel composition of claim 66 wherein said at least one melanin inhibiting agent comprises hydroquinone.

70. The skin peel composition of claim 66 wherein said at least one melanin inhibiting agent comprises arbutin.

71. The skin peel composition of claim 66 wherein said at least one melanin inhibiting agent comprises superoxide dismutase.

72. The skin peel composition of claim 66 wherein said skin exfoliation agent comprises at least one agent selected from the group consisting of salicylic acid, glycolic acid, and lactic acid.

73. The skin peel composition of claim 72 wherein said at least one melanin inhibiting agent comprises L-ascorbate.

74. The skin peel composition of claim 72 wherein said at least one melanin inhibiting agent comprises licorice root extract.

75. The skin peel composition of claim 72 wherein said at least one melanin inhibiting agent comprises hydroquinone.

76. The skin peel composition of claim 72 wherein said at least one melanin inhibiting agent comprises arbutin.

77. The skin peel composition of claim 72 wherein said at least one melanin inhibiting agent comprises superoxide dismutase.

78. The skin peel composition of claim 66 wherein said skin exfoliation agent comprises salicylic acid.

79. The skin peel composition of claim 78 wherein said at least one melanin inhibiting agent comprises L-ascorbate.

80. The skin peel composition of claim 78 wherein said at least one melanin inhibiting agent comprises licorice root extract.

81. The skin peel composition of claim 78 wherein said at least one melanin inhibiting agent comprises hydroquinone.

82. The skin peel composition of claim 78 wherein said at least one melanin inhibiting agent comprises arbutin.

83. The skin peel composition of claim 78 wherein said at least one melanin inhibiting agent comprises superoxide dismutase.

84. The skin peel composition of claim 66 wherein said skin exfoliation agent comprises glycolic acid.

85. The skin peel composition of claim 84 wherein said at least one melanin inhibiting agent comprises L-ascorbate.

86. The skin peel composition of claim 84 wherein said at least one melanin inhibiting agent comprises licorice root extract.

87. The skin peel composition of claim 84 wherein said at least one melanin inhibiting agent comprises hydroquinone.

88. The skin peel composition of claim 84 wherein said at least one melanin inhibiting agent comprises arbutin.

89. The skin peel composition of claim 84 wherein said at least one melanin inhibiting agent comprises superoxide dismutase.

90. The skin peel composition of claim 66 wherein said skin exfoliation agent comprises lactic acid.

91. The skin peel composition of claim 90 wherein said at least one melanin inhibiting agent comprises L-ascorbate.

92. The skin peel composition of claim 90 wherein said at least one melanin inhibiting agent comprises licorice root extract.

93. The skin peel composition of claim 90 wherein said at least one melanin inhibiting agent comprises hydroquinone.

94. The skin peel composition of claim 90 wherein said at least one melanin inhibiting agent comprises arbutin.

95. The skin peel composition of claim 90 wherein said at least one melanin inhibiting agent comprises superoxide dismutase.

96. The skin peel composition of claim 66 wherein said melanin inhibiting agent comprises both arbutin and licorice root extract.

97. The skin peel composition of claim 96 wherein said melanin inhibiting agent further comprises hydroquinone.

98. The skin peel composition of claim 66 wherein said melanin inhibiting agent comprises both kojic acid and licorice root extract.

99. The skin peel composition of claim 66 wherein said melanin inhibiting agent comprises both kojic acid and arbutin.

100. The skin peel composition of claim 66 wherein said melanin inhibiting agent comprises kojic acid and said composition further comprises glycyrrhizic acid.

101. The skin peel composition of claim 66 wherein said melanin inhibiting agent comprises both arbutin and hydroquinone.

* * * * *

UNITED STATES PATENT AND TRADEMARK OFFICE
CERTIFICATE OF CORRECTION

PATENT NO. : 6,710,076 B2 Page 1 of 3
DATED : March 23, 2004
INVENTOR(S) : Margaret M. Ancira It is certified that error appears in the above-identified patent and that said Letters Patent is hereby corrected as shown below:

Title page,
Item [56], References Cited, OTHER PUBLICATIONS, insert the following references:

Physician's Choice of Arizona, Inc. v. Rhonda Allison, an individual dba Rhonda Allison Skin Therapies and Rhonda Allison Clinical Enterprises, Case No. CIV99 2104 PHX SMM, U.S. District Court, District of Arizona, Final Judgment (Proposed), dated April 10, 2000

Physician's Choice of Arizona, Inc. v. Rhonda Allison, an individual dba Rhonda Allison Skin Therapies and Rhonda Allison Clinical Enterprises, Case No. CIV99 2104 PHX SMM, U.S. District Court, District of Arizona, Permanent Injunction (proposed), dated April 10, 2000

Physician's Choice of Arizona, Inc. v. Rhonda Allison, an individual dba Rhonda Allison Skin Therapies and Rhonda Allison Clinical Enterprises, Case No. CIV99 2104 PHX SMM, U.S. District Court, District of Arizona, Defendant's Original Answer and Demand for Jury Trial, dated January 26, 2000

Physician's Choice of Arizona, Inc. v. Rhonda Allison, an individual dba Rhonda Allison Skin Therapies and Rhonda Allison Clinical Enterprises, Case No. CIV99 2104 PHX SMM, U.S. District Court, District of Arizona, First Amended Complaint for Patent Infringement and Demand for Jury Trial, filed December 7, 1999

Physician's Choice of Arizona, Inc. v. Peter Thomas Roth Labs, L.L.C., Case No. CIV 99 2103 PHX PGR, U.S. District Court, District of Arizona, Stipulation for Entry of Final Judgment and proposed Final Judgment Order, dated February 2, 2001

Physician's Choice of Arizona, Inc. v. Peter Thomas Roth Labs, L.L.C., Case No. CIV 99 2103 PHX PGR, U.S. District Court, District of Arizona, Settlement Agreement between Physician's Choice of Arizona, Inc. and Peter Thomas Roth Labs, L.L.C. dated January 21, 2001

Physician's Choice of Arizona, Inc. v. Peter Thomas Roth Labs, L.L.C., Case No. CIV 99 2103 PHX PGR, U.S. District Court, District of Arizona, Defendant's Answer to First Amended Complaint and Counterclaim, dated May 3, 2000

Physician's Choice of Arizona, Inc. v. Peter Thomas Roth Labs, L.L.C., Case No. CIV 99 2103 PHX PGR, U.S. District Court, District of Arizona, Joint Case Management Report resulting from Court's "Order Setting Scheduling Conference" filed December 17, 1999

UNITED STATES PATENT AND TRADEMARK OFFICE
CERTIFICATE OF CORRECTION

PATENT NO. : 6,710,076 B2
DATED : March 23, 2004
INVENTOR(S) : Margaret M. Ancira It is certified that error appears in the above-identified patent and that said Letters Patent is hereby corrected as shown below:

OTHER PUBLICATIONS, cont'd.,

Physician's Choice of Arizona, Inc. v. Peter Thomas Roth Labs, L.L.C., Case No. CIV 99 2103 PHX PGR, U.S. District Court, District of Arizona, First Amended Complaint for Patent Infringement and Demand for Jury Trial, filed December 7, 1999

Physician's Choice of Arizona, Inc. v. SesDerma, Inc., Case No. CIV03 0260 PHX JAT, U.S. District Court, District of Arizona, Complaint, filed February 7, 2003

Physician's Choice of Arizona, Inc. v. Visual Changes Skin Care International, Inc., Case No. CIV03 0873 PHX RCB, U.S. District Court, District of Arizona, Complaint, filed May 9, 2003

CANNING, C., "The Skin Care Market, pgs. 14-15, May 1994

CoValence, Inc. Advertisement, CoValence, Inc. Firsts (1 pg.) (undated)

SERRANO SANMIGUEL, G., et al., "Melasma: Nuevas Perspectivas Para Un Viejo Problema," Dermocosmetica Clinica, Vol. 4 No. 4 (undated) (1 pg.)

SERRANO SANMIGUEL, G., et al., "Peeling Superficial Con Acido Glicolico Neutralizado: Un Concepto Nuevo de Peeling," Dermocosmetica Clinica, 4: 243-254 (handwritten "October 1993" notation provided by defendant) (12 pgs.)

SesDERMA brochure, "New Generation of Pigmentation Inhibitors" (undated) (4 pgs.)

SesDERMA brochure, "The Most Effective Solution to Melasma or Chloasma and Other Facial Pigmentations, Depigmenting Gel" (Hydroquin) (believed to be published in 2000 or later based on references at end) (3 pgs.)

SesDERMA brochure, "The New Generation of Pigmentation Inhibitors" on Hydroquin and Kojicol (undated) (4 pgs.)

Brody, Chemical Peeling, pp 53-73 (superficial peeling), 75-97 (medium depth peeling), and 165-170 (index) (1993)

UNITED STATES PATENT AND TRADEMARK OFFICE
CERTIFICATE OF CORRECTION

PATENT NO. : 6,710,076 B2
DATED : March 23, 2004
INVENTOR(S) : Margaret M. Ancira It is certified that error appears in the above-identified patent and that said Letters Patent is hereby corrected as shown below:

OTHER PUBLICATIONS, cont'd.,

KLIGMAN, A., M.D., Ph.D., "Results of a Pilot Study Evaluating the Compatibility of Topical Tretinoin in Combination with Glycolic Acid," Cosmetic Dermatology, pg. 29, Vol. 6, No. 10, October 1993 (first page only)

"El Lightening Peel Actua a la vez Sobre los Depositos de Melanina y en us Sintesis" (2 pgs) (undated)

NAKAGAWA, M., et al., "Contact Allergy to Kojic Acid in Skin Care Products", Contact Dermatitis (1995) (5 pgs.)

"Nuevos Peelings con AHAs, New Peels with AHA," Piel y Dermocosmetica IberoAmericana (handwritten "1997" notation provided by defendant)

SERRANO SANMIGUEL, G., Form No. 1036948 documenting the presentation of HIDROQUIN to the Direccion General De Farmacia Y Productos Sanitarios (Health Department) by Gabriel Serrano Sanmiguel (March 11, 1992) (1 pg.)

Signed and Sealed this

Twelfth Day of October, 2004

JON W. DUDAS
*Director of the United States Patent and Trademark Office*

Disclaimer

6,710,076 B2 — Margaret M. Ancira, Scottsdale, AZ. HYDROXY-KOJIC ACID SKIN PEEL. Patent dated Mar. 23, 2004. Disclaimer filed Feb. 11, 2005, by assignee, Physician's Choice of Arizona.

Hereby enters this disclaimer to claims 1-101 of said patent.

*(Official Gazette May 17, 2005)*